(12) United States Patent
Ternes

(10) Patent No.: US 7,532,924 B2
(45) Date of Patent: May 12, 2009

(54) CARDIAC RHYTHM MANAGEMENT SYSTEM WITH EXERCISE TEST INTERFACE

(75) Inventor: David Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 917 days.

(21) Appl. No.: 10/667,206

(22) Filed: Sep. 22, 2003

(65) Prior Publication Data

US 2005/0065443 A1 Mar. 24, 2005

(51) Int. Cl.
*A61N 1/362* (2006.01)
(52) U.S. Cl. .......................................... 600/523; 607/30
(58) Field of Classification Search .................. 600/508, 600/523–525, 519, 520, 513, 510; 607/17–19, 607/59, 30
See application file for complete search history.

(56) References Cited

U.S. PATENT DOCUMENTS

| | | | |
|---|---|---|---|
| 4,090,505 A | | 5/1978 | Mortara |
| 4,340,065 A | | 7/1982 | Gessman |
| 4,552,156 A | | 11/1985 | Jackson |
| 4,622,980 A | * | 11/1986 | Kunig ......................... 600/517 |
| 4,852,570 A | | 8/1989 | Levine |
| 4,883,063 A | * | 11/1989 | Bernard et al. .............. 600/483 |
| 5,007,431 A | | 4/1991 | Donehoo, III |
| 5,113,869 A | | 5/1992 | Nappholz et al. |
| 5,163,439 A | * | 11/1992 | Dardik ....................... 600/508 |
| 5,243,993 A | * | 9/1993 | Alexander et al. .......... 600/520 |
| 5,410,473 A | | 4/1995 | Kaneko et al. |
| 5,669,391 A | | 9/1997 | Williams |
| 5,706,822 A | * | 1/1998 | Khavari ...................... 600/483 |
| 5,749,367 A | * | 5/1998 | Gamlyn et al. .............. 600/509 |
| 5,772,601 A | | 6/1998 | Oka et al. |
| 5,817,027 A | | 10/1998 | Arand et al. |
| 5,840,039 A | * | 11/1998 | Heikkila ...................... 600/519 |
| 5,935,085 A | | 8/1999 | Welsh et al. |
| 5,980,464 A | | 11/1999 | Tsuda |
| 6,149,602 A | | 11/2000 | Arcelus |
| 6,169,919 B1 | | 1/2001 | Nearing et al. |

(Continued)

OTHER PUBLICATIONS

"Exercise Stress Testing Helps Identify People at Risk of Developing Coronary Heart Disease; Testing for Exercise Capacity, Heart Rate Recovery Improves on Traditional Risk-Factor Scoring", *AScribe Newswire*, http://www.ascribe.org/cgi-bin/behold.pl?ascribeid=20050913.075721&time=08%2038%20PDT&year=2005&public=1,(Sep. 13, 2005), 1-3.

(Continued)

*Primary Examiner*—George R Evanisko
(74) *Attorney, Agent, or Firm*—Schwegman, Lundberg & Woessner, P.A.

(57) ABSTRACT

This document discusses, among other things, cardiac rhythm management systems, devices, and methods providing an exercise test interface. A patient exercise episode is identified using at least one predetermined criteria. Data associated with the episode is obtained. A summary of the episode is displayed for a user. The displayed summary includes at least one prognostic indicator obtained from the data associated with the episode. Examples of prognostic indicators include, among other things, ectopic beats, runs of ectopic beats, rate of decrease of heart rate during a post-exercise recovery portion of the episode, a maximum attained heart rate for comparison to a maximum age-predicted heart rate, as well as other prognostic indicators.

42 Claims, 15 Drawing Sheets

U.S. PATENT DOCUMENTS

| | | | | |
|---|---|---|---|---|
| 6,823,213 | B1 * | 11/2004 | Norris et al. | 607/9 |
| 6,973,350 | B1 * | 12/2005 | Levine et al. | 607/27 |
| 7,155,278 | B2 * | 12/2006 | King et al. | 607/2 |
| 7,162,299 | B1 * | 1/2007 | Kroll et al. | 607/14 |
| 7,177,684 | B1 * | 2/2007 | Kroll et al. | 607/17 |

OTHER PUBLICATIONS

"Non-Invasive QT Dispersion Measurement", *GE Medical Systems*, http://www.gemedicalsystems.com/cgi-bin/print/print.cgi, (Archived Aug. 6, 2001), 4 Pages.

"Study: Heart after exercise test can predict death risk", CNN.com/Health, http://clinton.cnn.com/2003/HEALTH/conditions/02/27/heart.stress.tests.ap/, (Feb. 27, 2003), 2 Pages.

Andrade, J. C., "Cardiac Contractility Sensor Evaluation in a DDDR System—A Multicenter Study", *Progress in Biomedical Research*, 3(3), (Jun. 1998), 137-142.

Aytemir, Kudret, et al., "QT Dispersion plus ST-Segment Depression: A New Predictor of Restenosis after Successful Precutaneous Transluminal Coronary Angioplasty", *Clin. Cardiol.*, vol. 22, (Summary), (Jun. 1999), 409-412.

Greco, Enrico M., et al., "Clinical evaluation of peak endocardial acceleration as a sensor for rate responsive pacing", *Pacing and Clinical Electrophysiology*, vol. 26, Issue 4, Part 1, (Apr. 2003), 812-818.

Lee, Jong-Suk, et al., "Heart Rate Turbulence after Ventricular Premature Beats: It's Relation to Heart Rate Variability", *GE Medical Systems Korea, Education—Case Studies*, http://www.gemedicalsystems.com/krko/education/case_studies/Marquette/HRT.html, (Archived Jan. 17, 2003).

Mora, Samia, et al., "Enhanced Risk Assessment in Asymptomatic Individuals With Exercise Testing and Framingham Risk Scores", *Circulation*, 112(11), (Sep. 13, 2005), 1566-1572.

Naas, Abdul A., et al., "QT and QTc dispersion are accurate predictors of cardiac death in newly diagnosed non-insulin dependent diabetes: cohort study", *British Medical Journal*, 316(7133), (Mar. 7, 1998), 745-746.

"Study: Heart Stress Test Can Predict Risks", Heart1.com, http://www.heart1.com/news/mainstory_pr.cfm?newsarticle=81, (Feb. 27, 2003), 2 Pages.

Bell, Howard, "Fight or Flight: In weighing cardiac risk factors, doctors are overlooking autonomic tone", *Physician's Weekly*, vol. XIX, No. 13, http://www.physweekly.com/article.asp?issue=13&article=41&printable=1, (Apr. 1, 2002), 2 Pages.

Roa, Richard, "Current Trends in Patient Monitoring", http://bsp.pdx.edu/Seminar/2002/Spring/Roa.pdf, (May 21, 2002), 6 Pages.

* cited by examiner

US 7,532,924 B2

CARDIAC RHYTHM MANAGEMENT SYSTEM WITH EXERCISE TEST INTERFACE

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

This patent application pertains generally to cardiac rhythm management systems, and more particularly, but not by way of limitation, to a cardiac rhythm management system with an exercise test interface.

BACKGROUND

Implantable medical devices include, among other things, cardiac rhythm management (CRM) devices such as pacers, cardioverters, defibrillators, cardiac resynchronization therapy (CRT) devices, as well as combination devices that provide more than one of these therapy modalities to a patient. Such implantable devices are typically powered by a battery. Moreover, such implantable devices are typically communicatively couplable to an external programmer or other local or distant interface device, such as an advanced patient management (APM) system that is capable of communicating with the implantable device over a computer network and/or telephonic communications network. This allows the external programmer or APM system to be used for programming operational parameters of the implantable device or for receiving from the implantable device data about the patient or about the implantable device. The effects of exercise on a cardiac patient provides useful diagnostic and prognostic information about the cardiac patient.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

Figure 1:
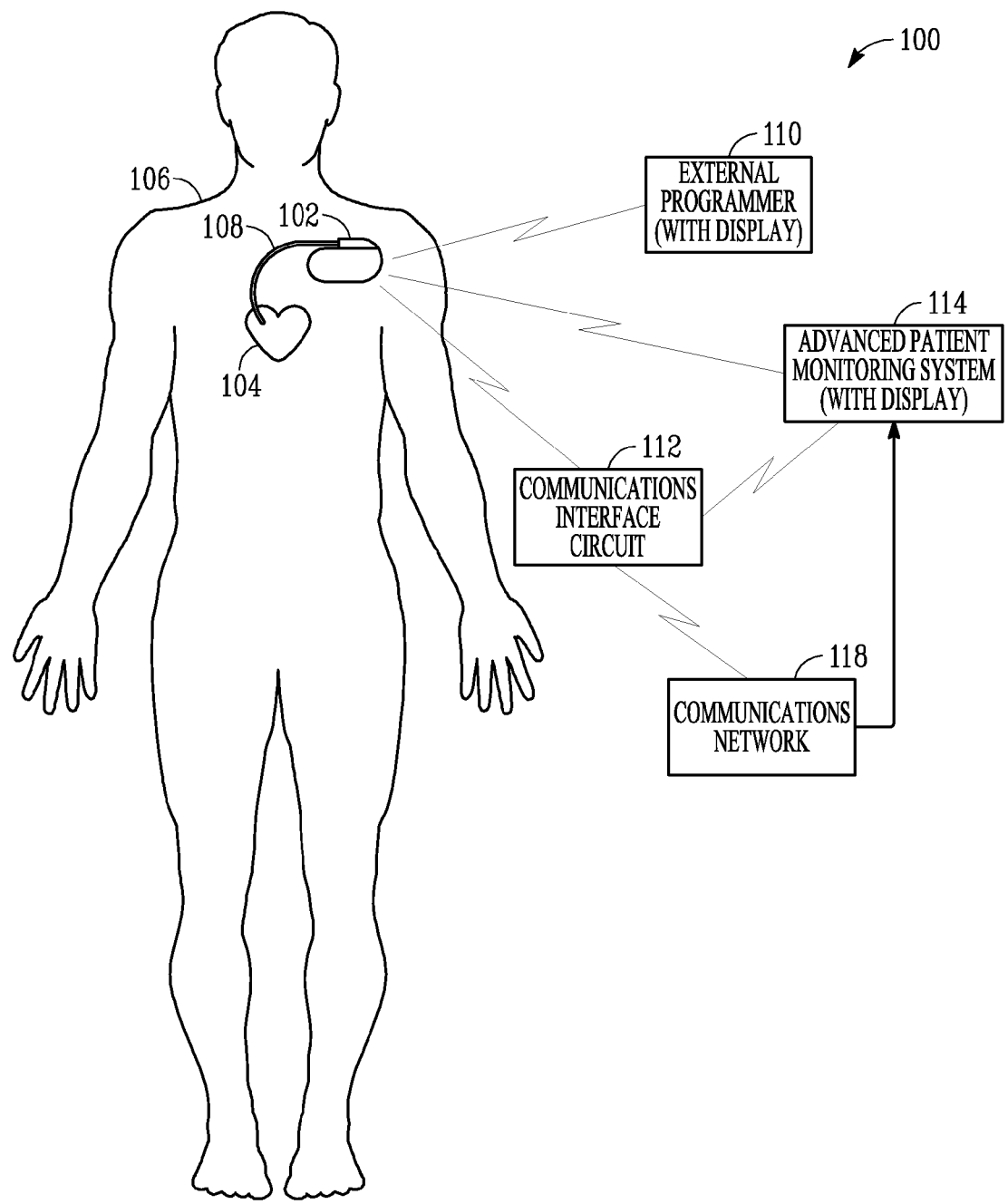
FIG. 1 is a schematic diagram illustrating generally one example of portions of a system including an exercise test interface.

FIG. 1 is a schematic diagram illustrating generally one example of portions of a system 100 including an exercise test interface. In the example of FIG. 1, the system 100 includes an implantable device 102, such as implantable cardiac rhythm management (CRM) device. The implantable device 102 is coupled to a heart 104 of a patient 106 by at least one leadwire 108, such as for sensing intrinsic electrical heart signals from the heart 104 and/or for delivering pacing, defibrillation, or other therapy to the heart 104. The implantable device 102 is communicatively coupled (e.g., using one or more of the communications links illustrated in FIG. 1) to an external device, such as to one or more of an external programmer 110, an external repeater or other communications interface circuit 112, or an advanced patient management (APM) system 114 that manages various such implantable devices 102 across various patients 106. In the example of FIG. 1, the communications interface circuit 112 serves as a repeater or other intermediary device for enabling communication between the implantable device 102 and the APM system 114. The system 100 may also include or use one or more other intermediary modes of communication, such as over a telephonic and/or computer communications network 118. As discussed below, the system 100 includes certain features that are useful in conjunction with an exercise test involving the patient 106 undergoing some activity (e.g., walking, biking, etc.) and a monitoring of the response of the patient's cardiovascular system 106 and/or operation of the implantable device 102 during the exercise test (which typically includes both an exercise portion and a post-exercise recovery portion that also provides useful information, as discussed below).

Figure 2:
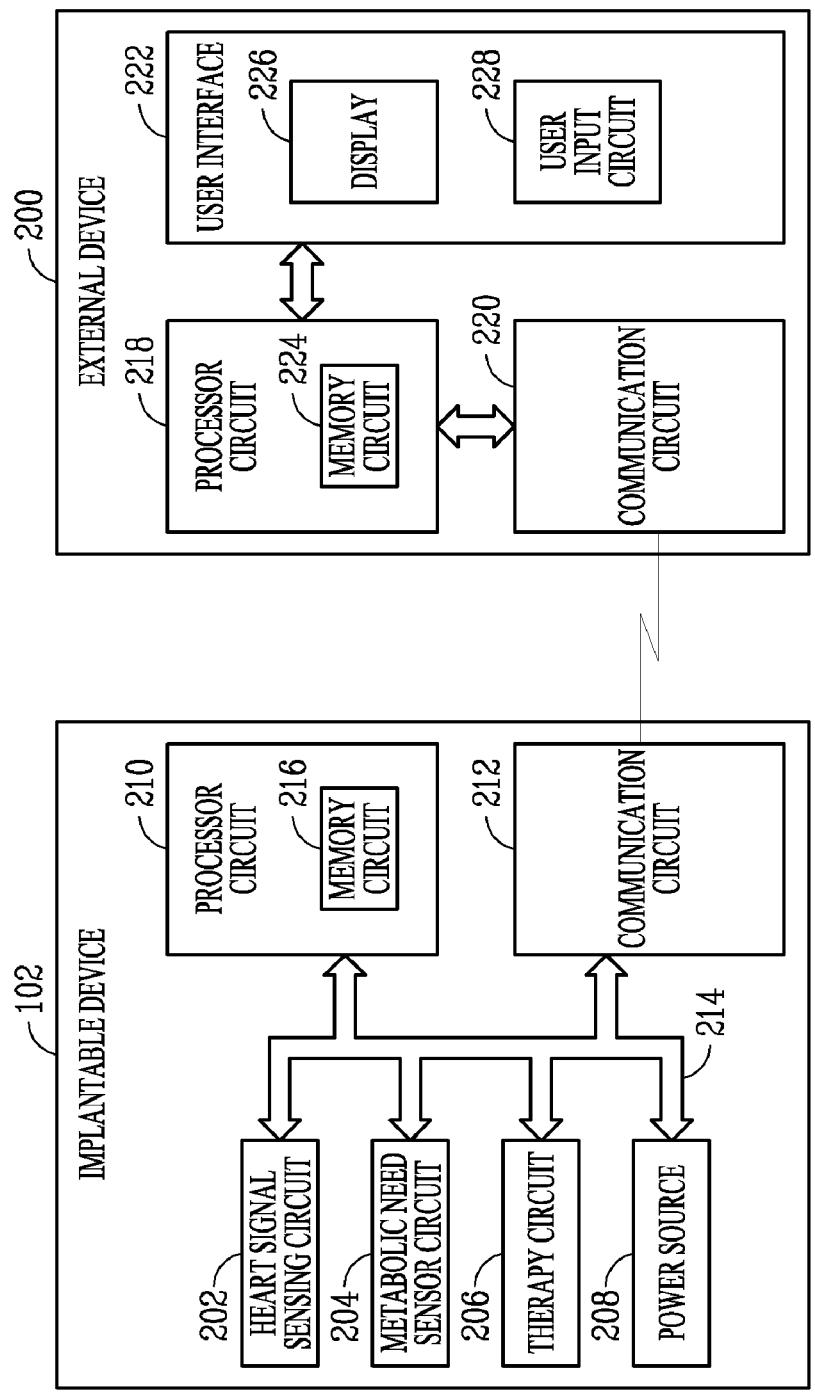
FIG. 2 is a block diagram illustrating generally one example of portions of an implantable device and an external device, such as one of an external programmer or an APM system.

FIG. 2 is a block diagram illustrating generally one example of portions of the implantable device 102 and an external device 200, such as one of the external programmer 110 or the APM system 114. In this example, the implantable device 102 includes, among other things, a heart signal sensing circuit 202, a metabolic need sensor circuit 204, a therapy circuit 206, a battery or other power source 208, a microprocessor or other processor circuit 210, and a communication circuit 212. One or more of these components are coupled to one or more others of these components using one or more interconnection wires and/or buses 214. In this example, the processor circuit 210 includes an on-board and/or off-chip memory circuit 216. The heart signal sensing circuit 202 typically includes sense amplifier(s) to sense an electrical intrinsic heart signal and depolarization detector(s) (e.g., a peak detector, a level detector, a morphology detector, etc.) to detect electrical heart depolarizations that accompany corresponding contractions of heart chamber(s). The metabolic need sensor circuit 204 typically includes a metabolic need sensor and associated signal processing circuitry for obtaining metabolic need information from the sensor output signal. The metabolic need sensor provides a sensor output indicative of a patient's need for a particular (e.g., higher or lower) cardiac output to support the patient's metabolic need for blood circulation. One example of a metabolic need sensor is an accelerometer. An accelerometer senses acceleration of the patient. At certain frequencies, the sensed acceleration is indicative of the patient's activity level and, therefore, is indicative of the patient's need for a particular cardiac output. Another example of a metabolic need sensor is a respiration (i.e., breathing) sensor, such as a minute ventilation (MV) sensor. The MV sensor provides information about the patient's breathing rate and/or tidal volume. Such information is correlative to a patient's activity and to the patient's need for a particular cardiac output. Other suitable examples of metabolic need sensors include, without limitation: an oxygen saturation sensor (such as an oxymeter), a myocardial contractility sensor, a QT-interval sensor, a stroke volume sensor, a blood temperature sensor, and a heart sound sensor.

In this example, the external device 200 includes a microprocessor or other processor circuit 218, a communication circuit 220, and a user interface device 222. In this example, the processor circuit 218 includes an on-board and/or off-chip memory circuit 224. The user interface 222 includes a viewing screen or other display 226. In this example, the user interface 222 also includes a user input circuit 228, such as a computer keyboard, a mouse, a voice recognition circuit, and/or any other device capable of receiving input from a physician, the patient 106, or another user. As discussed below, the display 226 includes certain features that are useful with an exercise test, such as for monitoring the response of the patient's cardiovascular system and/or operation of the implantable device 102 during the exercise test.

Figure 3:
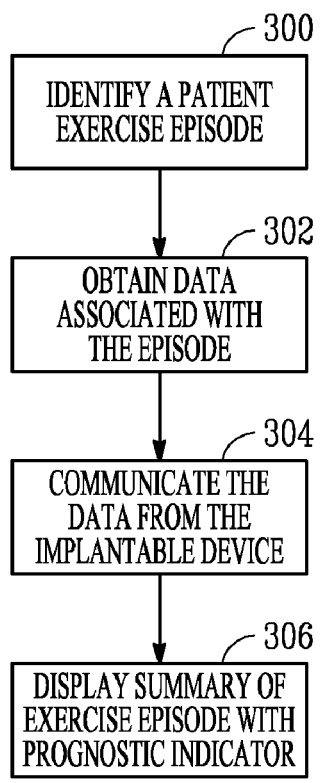
FIG. 3 is a flow chart illustrating generally one example of a method of providing a physician or other user with information regarding an exercise episode by a patient.

FIG. 3 is a flow chart illustrating generally one example of a method of providing a physician or other user with information regarding an exercise episode by the patient 106. The exercise episode may be a formally prescribed exercise test (e.g., putting the patient 106 on a treadmill or other exercise regimen in a doctor's office). Alternatively, the exercise episode may involve unsupervised activity by the patient 106 on his or her own accord (e.g., walking, running, climbing stairs, or engaging in any other day-to-day activity). In either case, the exercise episode may include both an exercise portion (e.g., during which time the patient's heart rate increases or subsequently remains elevated) and a post-exercise recovery portion (e.g., during which time the patient's heart rate declines back to a baseline non-exercise level).

In FIG. 3, at 300 a patient exercise episode is identified using at least one predetermined criteria that defines whether an exercise episode is occurring. At 302, data associated with the episode is obtained from the patient by the implantable device 102. At 304, the exercise episode data is communicated from the implantable device 102 (either before or after processing the data to obtain useful information about the exercise episode, as discussed below). At 306, the processed data is used to display a summary of the exercise episode for the user. In one example, this displayed summary includes at least one prognostic indicator, as discussed below.

Figure 4:
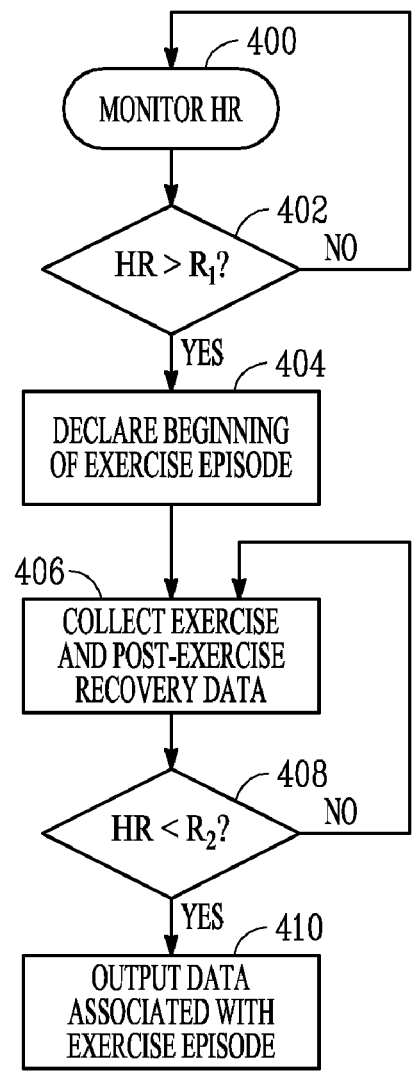
FIG. 4 is a flow chart illustrating generally, among other things, one example of identifying an exercise episode using at least one predetermined criteria.

FIG. 4 is a flow chart illustrating generally, among other things, one example of identifying an exercise episode using at least one predetermined criteria as discussed above with respect to 300. In the example of FIG. 4, the at least one predetermined criteria includes at least one patient heart rate (HR) to define the beginning and/or the end of the exercise episode. In FIG. 4, at 400 heart rate is monitored, such as by using the heart signal sensing circuit 202 to sense an electrical intrinsic heart signal from the patient 106. The heart signal includes sensed and/or paced heart depolarizations. The processor 210 uses the time intervals between such heart depolarizations to compute the subject's beat-to-beat heart rate. At 402, the heart rate is compared to a programmable exercise onset rate threshold R1. In this example, when the HR climbs above the exercise onset rate threshold R1, then an exercise episode is declared at 404, and the implantable device 102 begins at 404 collecting data associated with the exercise episode; otherwise the implantable device 102 continues to monitor the heart rate at 400. In this example, after the beginning of an exercise episode has been declared at 404, the implantable device 102 collects, at 406, exercise data at (associated with a rising and/or elevated heart rate) and post-exercise recovery data (associated with a heart rate declining back toward a resting value). In one example, to declare an end of the exercise episode, at 408 the heart rate is compared to a programmable exercise ending rate threshold, R2, which may be programmed to the same value as the exercise onset threshold R1, or to a different value). When the heart rate falls below the exercise ending rate threshold R2, then the end of the exercise episode is declared and the implantable device 102 stops collecting data associated with the exercise episode (although it may continue collecting data for other purposes). At 410, data associated with the exercise episode is output, such as for storage in the memory circuit 216, or to the communication circuit 212 for communication from the implantable device 102 to the external device 200. Processing of the exercise episode data for producing the displayable exercise episode summary may be carried out either partially or fully within the implantable device 102 or, alternatively, by the external device 200, or by some combination thereof. In the example of FIG. 4, the thresholds R1 and R2 may be independently programmable to fixed values or, alternatively, either or both may be defined in terms of an incremental value above a resting or baseline heart rate determined from that patient, or from a population of other patients.

Figure 5:
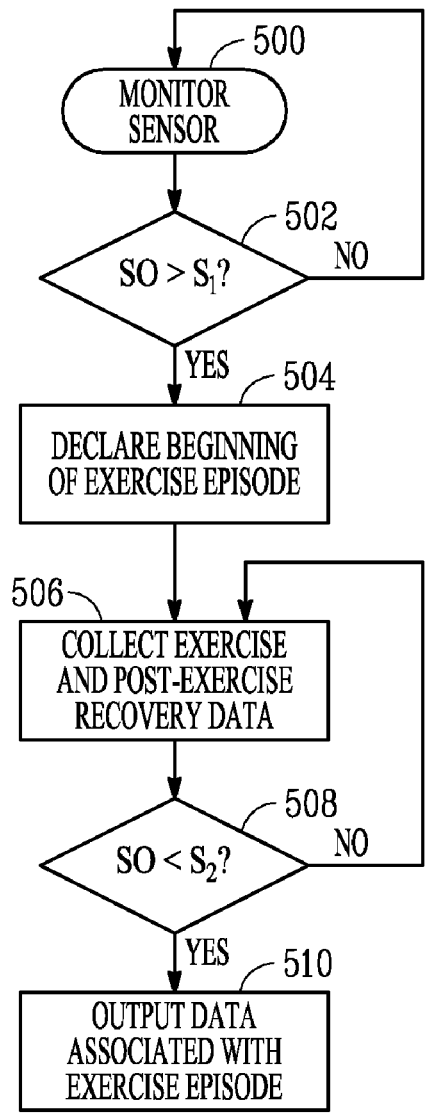
FIG. 5 is a flow chart illustrating generally, among other things, another example of identifying an exercise episode using at least one predetermined criteria.

FIG. 5 is a flow chart illustrating generally, among other things, another example of identifying an exercise episode using at least one predetermined criteria as discussed above with respect to 300. In the example of FIG. 5, the at least one predetermined criteria includes the sensor output (SO) of at least one metabolic need sensor to define the beginning and/or the end of the exercise episode. In FIG. 5, at 500 a metabolic need sensor output is monitored. This includes using the metabolic need sensor circuit 204 to sense an indication of the metabolic need of the patient for a particular (e.g., higher or lower) heart rate to obtain a needed cardiac output. At 502, the SO is compared to a programmable exercise onset sensor output threshold S1. In this example, when the sensor output climbs above the exercise onset sensor output threshold S1, then an exercise episode is declared at 504, and the implantable device 102 begins collecting data associated with the exercise episode at 504; otherwise the implantable device 102 continues to monitor the metabolic need sensor output at 500. In this example, after the beginning of an exercise episode has been declared at 504, the implantable device 102 collects, at 506, exercise data (associated with a rising and/or elevated sensor output) and post-exercise recovery data (associated with a sensor output declining back toward a resting value). In this example, to declare an end of the exercise episode, at 508 the SO is compared to a programmable exercise ending sensor output threshold, S2, which may be programmed to the same value as the exercise onset threshold S1, or to a different value). When the metabolic need sensor output falls below the exercise ending sensor output threshold, S2, then the end of the exercise episode is declared and the implantable device 102 stops collecting data associated with the exercise episode (although it may continue collecting data for other purposes). At 510, data associated with the exercise episode is output, such as for storage in the memory circuit 216, or to the communication circuit 212 for communication from the implantable device 102 to the external device 200. Processing of the exercise episode data for producing the displayable exercise episode summary may be carried out either partially or fully within the implantable device 102 or, alternatively, by the external device 200, or by some combination thereof. In the example of FIG. 5, the thresholds S1 and S2 may be independently programmable to fixed values or, alternatively, may be defined in terms of an incremental value above a resting or baseline sensor output, e.g., determined from the patient, or from a population of other patients.

Moreover, the thresholds S1 and S2 need not be associated with the same sensor output. In one such illustrative example, an accelerometer sensor output is compared to the exercise onset threshold S1 (because motion is a good indication of the onset of exercise) and a minute ventilation (or other respiration sensor) output is compared to the exercise ending threshold S2 (because elevated breathing persists after active exercise during the recovery period). In another example, an accelerometer sensor output and a minute ventilation (or other respiration sensor) output are blended, and the blended sensor output is compared to one or both of the thresholds S1 and S2.

In one embodiment, the onset of the exercise episode is determined by comparing an accelerometer sensor output to an exercise onset threshold S1. In this embodiment, the onset of the recovery portion of the exercise episode is determined from the heart rate (i.e., heart rate hits a maximum heart rate value and then begins to decrease). The end of the exercise episode (and the end of the recovery period) is determined by comparing a minute ventilation (or other respiration sensor) to the exercise ending threshold S2.

In general, however, the onset of the exercise threshold can be determined from any one or more of the heart rate detector, the metabolic need sensor (e.g., accelerometer, minute ventilation, etc.) output, a user-provided trigger etc., and the onset of the recovery period can similarly be determined from any one or more of the heart rate detector, the metabolic need sensor (e.g., accelerometer, minute ventilation, etc.) output, a user-provided trigger, etc., and the ending of the exercise episode and the recovery period can be determined from any one or more of heart rate detector, the metabolic need sensor (e.g., accelerometer, minute ventilation, etc.) output, a user-provided trigger, etc., or by using a timer for measuring elapsed time from either the onset of the recovery period, or from the onset of the exercise period.

In each of the examples illustrated in FIGS. 4 and 5, the ending of the exercise episode can alternatively be declared by the timeout of a timer that was activated when the exercise episode onset was declared. In this example, the exercise episode for which data is collected will last a fixed period from its onset, regardless of whether the heart rate and/or sensor output continues to exceed the corresponding exercise ending threshold value. The appropriate time interval may be set according to how long exercise episodes usually last, or how much storage is available, or using any other appropriate factor.

Figure 6:
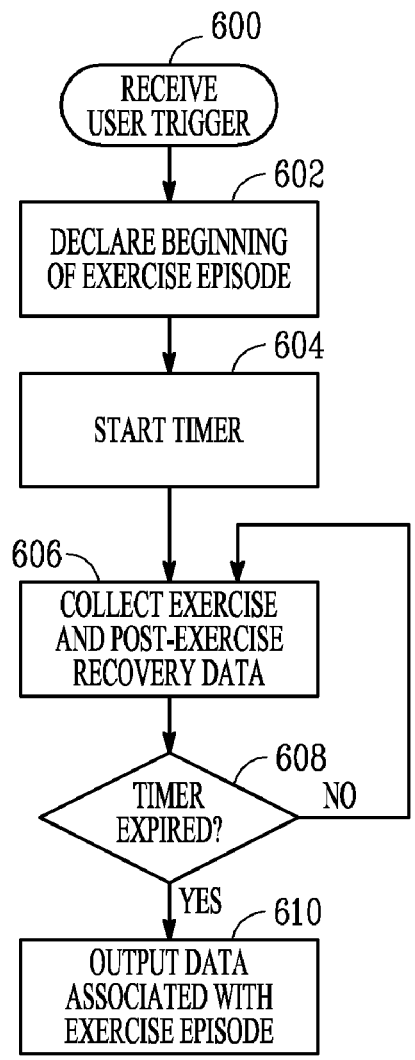
FIG. 6 is a flow chart illustrating generally, among other things, another example of identifying an exercise episode using at least one predetermined criteria.

FIG. 6 is a flow chart illustrating generally, among other things, another example of identifying an exercise episode using at least one predetermined criteria as discussed above with respect to 300. In the example of FIG. 6, the at least one predetermined criteria is a user-provided trigger at 600 that identifies the onset of the exercise episode at 602. One example of the user-provided trigger includes receiving input from a physician or other caregiver, or the patient, at the user input circuit 228, such as by using a mouse to on an icon of the display 226 to initiate the exercise episode. Another example of the user-provided trigger includes placing a magnet near the patient in close proximity of the implantable device 102 to close a reed switch in the implantable device, where the reed switch is coupled to a pin of the processor circuit 210 to provide an interrupt that initiates the exercise episode. In the example of FIG. 6, a declared beginning of the exercise episode starts a timer at 604. At 606, data is collected during exercise and post-exercise recovery portions of the declared exercise episode until the timer expires at 608. At 610, data associated with the exercise episode is output, such as for storage and/or communication to the external device 200 from the implantable device 102. As an alternative to using the timer to end the exercise episode, in other examples, the exercise episode is concluded by another user trigger (e.g., a mouse-click via user input circuit 228 or a magnet over the implantable device 102, etc.), or by one of the techniques described above with respect to FIGS. 4-5.

For the examples discussed in this document, data is collected during the exercise episode, which typically includes an exercise portion and a post-exercise recovery portion. One example of such data that is collected includes an electrocardiogram (ECG) signal, which indicates intrinsic heart activity. From the ECG signal a heart rate is extracted between atrial heart depolarizations and/or between ventricular heart depolarizations. In one example, useful prognostic information is also extracted from such intrinsic heart rate data. As discussed below, such useful prognostic information may include, among other things, one or more of: (1) a maximum heart rate obtained during the exercise episode (e.g., for comparing against a maximum age-predicted heart rate); and (2) a rate of decrease of the heart rate during the post-exercise recovery portion of the exercise episode. This is useful prognostic information for a doctor. For example, a cardiac patient that, during a sufficiently strenuous exercise test, cannot obtain close to his or her maximum age-predicted heart rate is expected to have a greater predicted likelihood of mortality. Similarly, a cardiac patient whose heart rate doesn't return quickly enough to the baseline resting heart rate after strenuous exercise is expected to have a greater predicted likelihood of mortality.

In another example, the intrinsic heart activity signal also provides information about arrhythmic heart beats. In one example, as discussed below, any ectopic intrinsic heart beats occurring during the exercise episode are identified. Unlike normal intrinsic heart beats, ectropic intrinsic heart beats do not originate from the normal firing of the heart's sinoatrial node. Any one or more of several techniques are used to identify such ectopic beats (also referred to as premature ventricular contractions, or PVCs). One technique (e.g., in a single chamber cardiac rhythm management device) includes using a time interval since the last beat was detected in the same heart chamber. If the time interval is shorter than a threshold value, the latter beat is classified as ectopic. Another technique (e.g., in a dual chamber cardiac rhythm management device) includes detecting ectopic ventricular beats as an intrinsic ventricular beat occurring without a corresponding preceding atrial beat. Yet another technique includes using a morphology of the electrical heart signal corresponding to a beat to distinguish an ectopic ventricular beat from a normal ventricular heart beat resulting from conduction of an atrial electrical heart beat signal through the atrioventricular node. A beat that is sufficiently different (e.g., by statistical analysis or other morphology techniques) from a templated normal beat is classified as ectopic. Signals from surface ECG electrodes and/or implanted electrodes can be used for such a morphology-based classification of ectopic beats. These techniques can be used in combination with each other and/or any other technique for detecting ectopic beats.

In one example, useful prognostic information is obtained from the data about ectopic heart beats occurring during the exercise episode, such as during the exercise portion of the exercise episode, and/or during the post-exercise recovery portion of the exercise episode.

In a further example, heart rate variability (HRV) information during the exercise episode is collected. For example, the HRV during the exercise episode may be compared to HRV information collected outside the exercise episode. HRV information during the exercise test provides another useful prognostic indicator. HRV during exercise is believed to reflect how the patient's cardiac output is influenced by the physical stress of exercise. During exercise, the patient's sympathetic and parasympathetic nervous systems may not be properly adjusting the cardiac output. Therefore, it is believed that monitoring HRV during exercise may provide useful information to a physician or other caregiver.

In yet another example, T-wave alternans (i.e., T-wave present on alternating sequential heart beats) information is collected during the exercise episode. T-wave alternans is believed to be a predictor of sudden cardiac death. Because, in some patients, the onset of T-wave alternans is rate-dependent, information about the rate above which T-wave alternans occurs is also collected.

In another example, information about heart rate turbulence (HRT) is collected during the exercise episode. HRT is one physiological response of a sinus node of a heart to PVCs. Heart rate turbulence is often manifested as a short initial acceleration in heart rate followed by a de-acceleration of the heart rate.

In another example, information about QT interval dispersion is collected during the exercise episode. Such QT interval dispersion quantifies the degree of myocardial repolarization inhomogeneity, such as by measuring a range of time-measurements from a Q-wave to a T-wave (of the same heart contraction) over a period of time.

In another example, information about the occurrence of paroxysmal atrial tachyarrhythmia (PAT) during the exercise episode is collected. PAT is typically due to a reentrant supraventricular tachyarrhythmia (e.g., AV nodal reentry, bypass tract-mediated macroreentry, intraatrial reentry, SA nodal reentry, etc.) Additionally, atrial flutter and/or atrial fibrillation may also be considered to be PAT, although atrial flutter and/or atrial fibrillation are usually categorized separately. In one example, PAT, atrial flutter, and/or atrial fibrillation that occurs during exercise are noted and indicated, since these abnormalities are risk factors for stroke or more serious tachyarrhythmias. Therefore, presenting such information to a physician or other caregiver should assist in diagnosis and/or treatment.

The exercise episode data is processed either by the implantable device 102, or by the external device 200, or using a combination of both. A summary of the exercise episode is displayed for the user on the display 226. In one example, the displayed exercise episode summary includes at least one prognostic indicator that indicates to the physician or other user how the cardiac patient is expected to fare in the future. Such information is useful to the physician for evaluating different treatment options.

Figure 7:
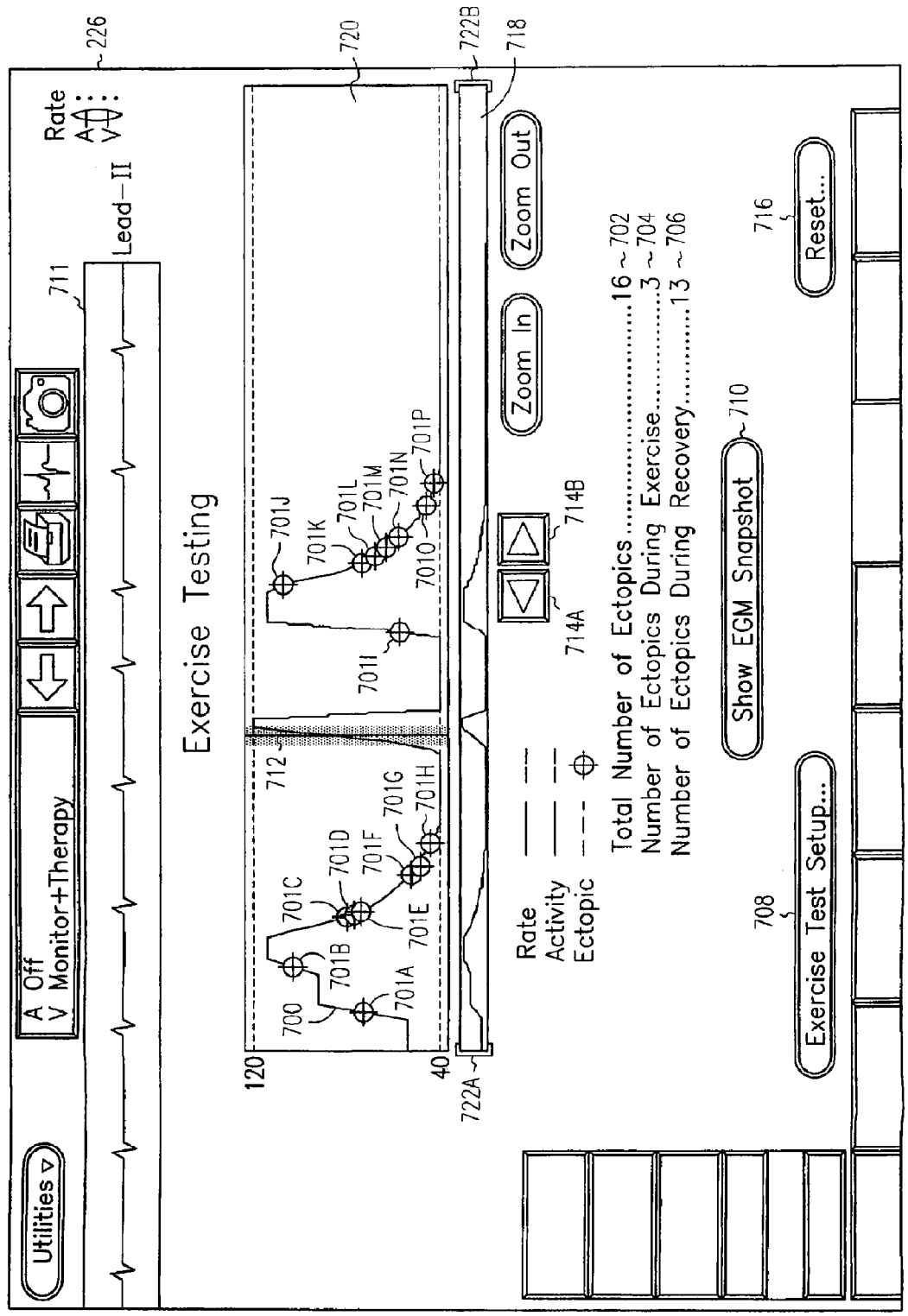
FIG. 7 is a screenshot illustrating generally one example of exercise episode summary information presented to a user via a display.

FIG. 7 is a screenshot illustrating generally one example of exercise episode summary information presented to the user via the display 226. In the example of FIG. 7, the display 226 includes a heart rate vs. time graph 700 during the exercise episode. In this example, the graph 700 also includes crosshairs or other indicators 701 of instances of ectopic beats occurring during the exercise episode, such as during the exercise portion of the exercise episode (when the heart rate is increasing to remaining at an elevated level after such an increase) and during the post-exercise recovery portion of the episode (when the heart rate decreases back toward the resting baseline heart rate after the exercise portion of the exercise episode). Such ectopic beats occurring during the exercise and/or port-exercise recovery portions of the exercise episode provide the physician with an important indicator of the prognosis of the particular patient from whom such data is gathered. Patients having a greater number of such ectopic beats during the exercise and particularly during the post exercise portion of the exercise episode are expected to have a poorer predicted mortality rate than patients not exhibiting such ectopic beats.

Accordingly, the display 226 presents a alphanumeric/textual summary of the ectopic data for the exercise episode, such as illustrated below the graph 700 in FIG. 7. In the example of FIG. 7, this includes an indicator 702 of the "Total Number of Ectopics" occurring during the exercise episode (e.g., in the example of FIG. 7, there were 16 ectopics that occurred during the exercise episode). The example of FIG. 7 also provides an indicator 704 of the "Number of Ectopics During Exercise" and a separate indicator 706 of the "Number of Ectopics During Recovery," because such separate indications have clinical significance to the physician as prognostic indicators of the cardiac patient's future likelihood of experiencing sudden cardiac death.

In this regard, runs of two sequential ectopic beats, three sequential ectopic beats, etc., are believed even more predictive of the patient's future likelihood of experiencing sudden cardiac death. Therefore, in a further example, such sequential runs of ectopics are also identified and displayed for the user. One such technique involves using the similar ectopic indicators 701, as illustrated in FIG. 7, but color-coding or otherwise distinguishing the indicators such that different colors (or other distinguishing features) represent different numbers of sequentially occurring ectopic beats. A color-coded or other table is displayed to assist the user in interpreting such information. For example, black could represent a single ectopic beat, blue could represent two sequential ectopic beats in a row, red could represent three or more sequential ectopic beats in a row, etc. Similarly, the textual/alphanumeric indicators 702, 704, and 706 could, in this example, be accompanied by other textual/alphanumeric indicators indicating "Total Number of Two Sequential Ectopics," "Total Number of Two Sequential Ectopics During Excercise," "Total Number of Two Sequential Ectopics During Recovery," "Total Number of Three or More Sequential Ectopics," "Total Number of Three or More Sequential Ectopics During Exercise," "Total Number of Three or More Sequential Ectopics During Recovery," etc. Such separate classification need not be limited to three or more sequential ectopic beats, but could be extended to differentiate between three sequential ectopics, four sequential ectopics, five sequential ectopics, etc.

The example of FIG. 7 also includes a "Exercise Test Setup" button 708. Clicking on this button using a mouse or like device triggers display of exercise test setup parameters that are configurable by the user. In one example, one such parameter defines what triggers the beginning of the exercise episode (e.g., heart rate exceeding a threshold, sensor output exceeding a threshold, a user-trigger from the external device 200, a magnet placed near the implantable device 102, etc.). In another example, another such parameter defines what triggers the end of the exercise episode (e.g., expiration of a timer, heart rate falling below a threshold, sensor output falling below a threshold, a user-trigger from the external device 200, a magnet placed near the implantable device 102, etc.). In a further example, another such parameter defines the length of the exercise episode, that is, how long the exercise data will be collected from the beginning of the exercise episode, such as where the end of the exercise episode is defined to result from the expiration of a timer. In one example, this length of time may depend on how much storage capacity is available to store and process the collected data for display. Other user-programmable exercise episode parameters determine what exercise episode summary information is presented to the user (e.g., the locations of the ectopics in the heart rate vs. time graph, textual information about the number of ectopics (and/or runs of ectopics) occurring during the exercise and post exercise recovery portions of the exercise episode, a graphically indicated heart rate recovery rate, a textual/alphanumeric indicated heart rate recovery rate, a graphical and/or textual/alphanumeric indication of age-predicted heart rate, a graphical and/or textual/alphanumeric indication of the maximum heart rate actually obtained during the exercise episode, etc.)

The example of FIG. 7 also includes a user-clickable "Show EGM Snapshot" button 710. Clicking on this button triggers display of the beat-to-beat electrocardiogram (ECG) heart activity signal 711 information during the exercise episode. In one example, this operates in conjunction with a slidable cursor line/bar 712, which is movable by directional buttons 714A-B. This allows the physician to select a particular time window during the exercise episode for displaying more detailed information, such as specific beat-by-beat ECG signal information. The example of FIG. 7 also includes a user-clickable "Reset" button 716 to flush the exercise summary data, such as in preparation for another exercise episode to be monitored and summarized. The example of FIG. 7 also includes (1) an overall view window 718 that displays graphed heart rate vs. time data over the entirety of the exercise episode, and (2) a zoomable window 720 that can be adjusted to show only a portion of the exercise episode, such as by using a mouse cursor for sliding the end brackets 722A-B of the overall view window to select the appropriate time window for viewing in the zoomable window 720.

Figure 8:
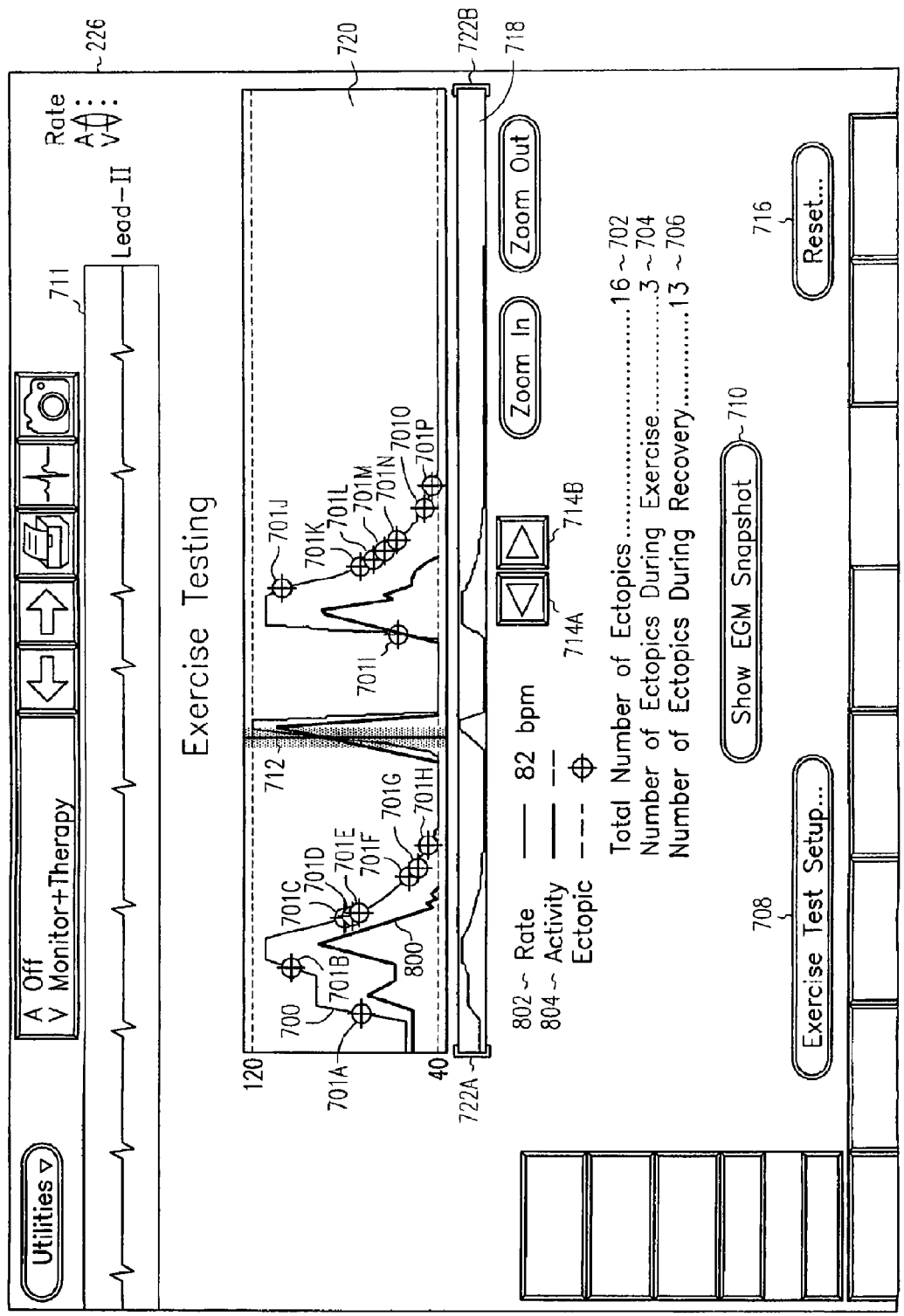
FIG. 8 is a screenshot illustrating generally a further example of exercise episode summary information presented to the user via a display, including a graph of a sensor output vs. time.

FIG. 8 is a screenshot illustrating generally a further example of exercise episode summary information presented to the user via the display 226, similar to FIG. 7. FIG. 8 also includes a graph 800 of a metabolic need sensor output vs. time. In this example, the sensor output vs. time graph 800 is presented in visual correspondence with the heart rate vs. time graph 700. Examples of the sensor output include a signal-processed accelerometer output that is indicative of the patient's activity (which is correlative to the patient's metabolic need for cardiac output), a respiration sensor, such as a minute ventilation (MV) sensor that is indicative of the patient's breathing (which is also correlative to the patient's activity and to the patient's metabolic need for cardiac output), and/or any other metabolic need sensor output, or any combination blending more than one such sensor outputs. The example of FIG. 8 includes an indication 802 of the instantaneous value of heart rate corresponding to the location on the graph 700 that is intersected by the slidable cursor line/bar 712, and an indication 804 of the instantaneous sensor output value corresponding to the location on the graph 800 that is also intersected by the slidable cursor line/bar 712.

Figure 9:
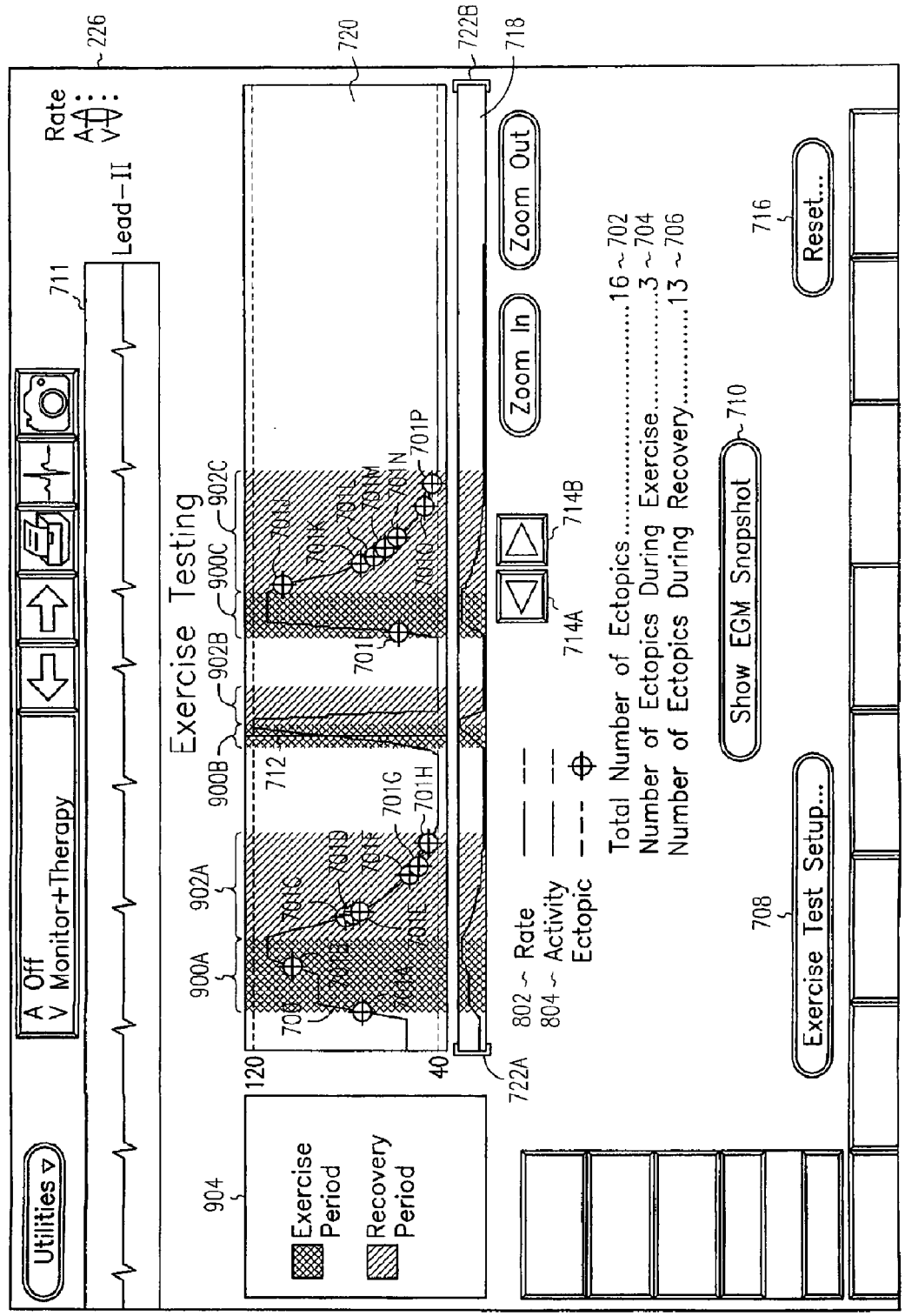
FIG. 9 is a screenshot illustrating generally a further example of exercise episode summary information presented to the user via a display, and including a highlighting indication to distinguish between exercise and recovery portions of the exercise episode.

FIG. 9 is a screenshot illustrating generally a further example of exercise episode summary information presented to the user via the display 226, similar to FIGS. 7-8. FIG. 9 also includes a highlighting indication, such as different background colors, to distinguish between exercise and recovery portions of the exercise episode. More particularly, exercise portions 900 (where heart rate is increasing or subsequently remaining elevated after such increase) are marked with a first background color (e.g., yellow) while recovery portions 902 (where heart rate is decreasing back toward a resting value) are marked with a different second background color (e.g., green). This assists the physician in distinguishing between exercise and recovery portions of the exercise episode, which is useful because events (e.g., ectopics) occurring during post-exercise recovery may have different prognostic significance than such events occurring during exercise portions of the exercise episode. FIG. 9 also includes a color coded index 904 to inform the user of what the different color backgrounds correspond to (e.g., that yellow corresponds to exercise, green corresponds to recovery, etc.).

Figure 10:
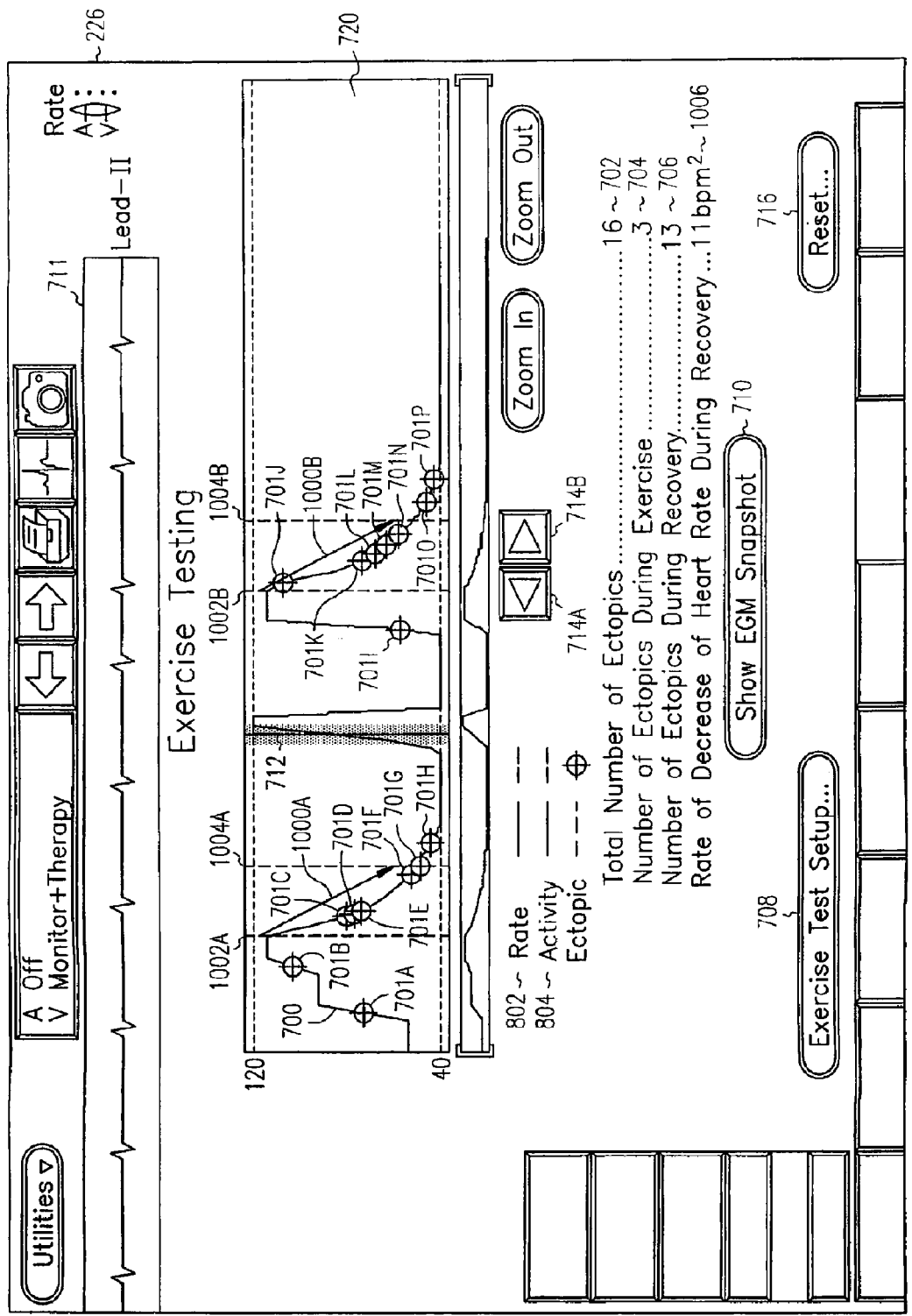
FIG. 10 is a screenshot illustrating generally a further example of exercise episode summary information presented to a user via a display, and including at least one indication of how fast a heart rate returns toward a resting value during a post-exercise recovery period.

FIG. 10 is a screenshot illustrating generally a further example of exercise episode summary information presented to the user via the display 226, similar to FIGS. 7-9. FIG. 10 also includes at least one indication of how fast the heart rate returns toward a resting value during the post-exercise recovery period. As discussed above, this provides a prognostic indicator of the cardiac patient's likelihood of experiencing future sudden cardiac death, with a slower recovery rate representing a greater likelihood of future sudden cardiac death. The heart rate recovery rate information can be presented in numerous ways. One technique of displaying such information is to draw a line 1000 extending from the beginning 1002 of the recovery period to the end 1004 of the recovery period. The slope of the line 1000 graphically illustrates the average time rate of change of the heart rate during the recovery period. In the example of FIG. 10, the first line 1000A during a first recovery period (between 1002A and 1004A) corresponds to a recovery rate magnitude of 20 beats/minute$^2$, the second line 1000R during a second recovery period (between 1002B and 1004B) corresponds to a slower recovery rate magnitude of 11 beats/minute$^2$. In one example, the recovery rate is compared to a predetermined threshold value. If the recovery rate falls below the predetermined threshold value (e.g., 13 beats/minute$^2$, in this illustrative example), then the color of the sloped line 1000 indicating recovery rate is changed (e.g., to red). This calls the user's attention to a potential increased risk of sudden cardiac death indicated for the particular patient as the result of a too-slow recovery rate extracted from that patient during the exercise test. In this example, FIG. 10 also illustrates a textual/alphanumeric indicator 1006 of the "Rate of Decrease of Heart Rate During Recovery." Because there may be more than one recovery portion of the exercise episode, in one example, the rate of decrease indicated by the textual/alphanumeric indicator 1006 corresponds to the particular recovery portion that is selected by the user by moving the slidable cursor line/bar 712 to overlay that particular recovery portion of the exercise episode.

Figure 11:
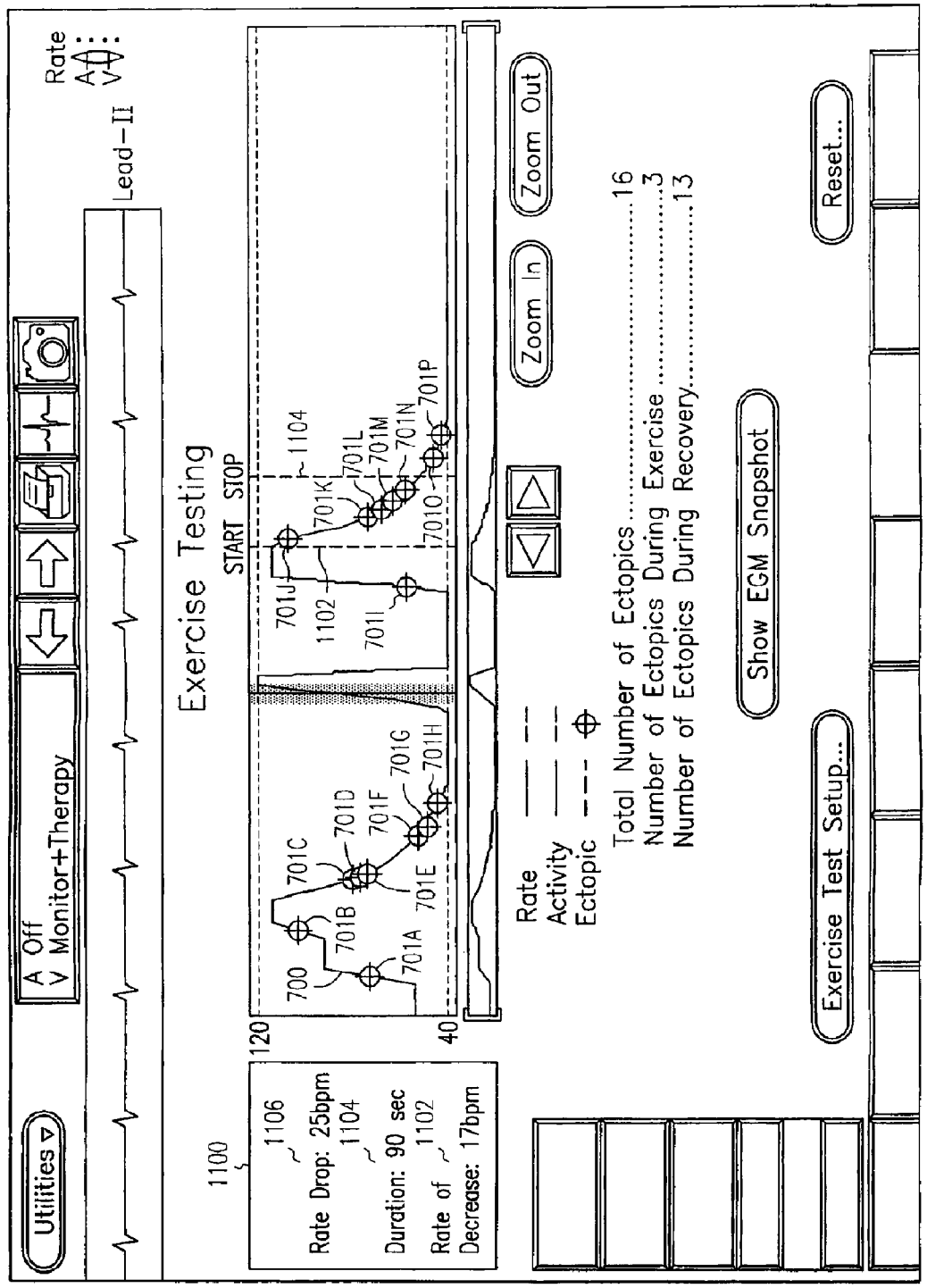
FIG. 11 is a screenshot illustrating generally a further example of exercise episode summary information presented to a user via a display, wherein the user can select the particular time period within the exercise episode over which the slope calculation is performed.

FIG. 11 is a screenshot illustrating generally a further example of exercise episode summary information presented to the user via the display 226, similar to FIGS. 7-10. In the example FIG. 11, the start lines 1002 and end lines 1004 are manipulable by the user (e.g., by dragging a cursor). This permits the user to select the particular time period within the exercise episode over which the slope calculation is performed. This also triggers a pop-up window 1100 that displays a textual/alphanumeric indication 1102 of the rate of change of the heart rate, a textual/alphanumeric indication 1104 of the time duration over which the slope calculation was performed, and a textual/alphanumeric indication 1106 of the absolute change in heart rate during the selected time interval.

Figure 12:
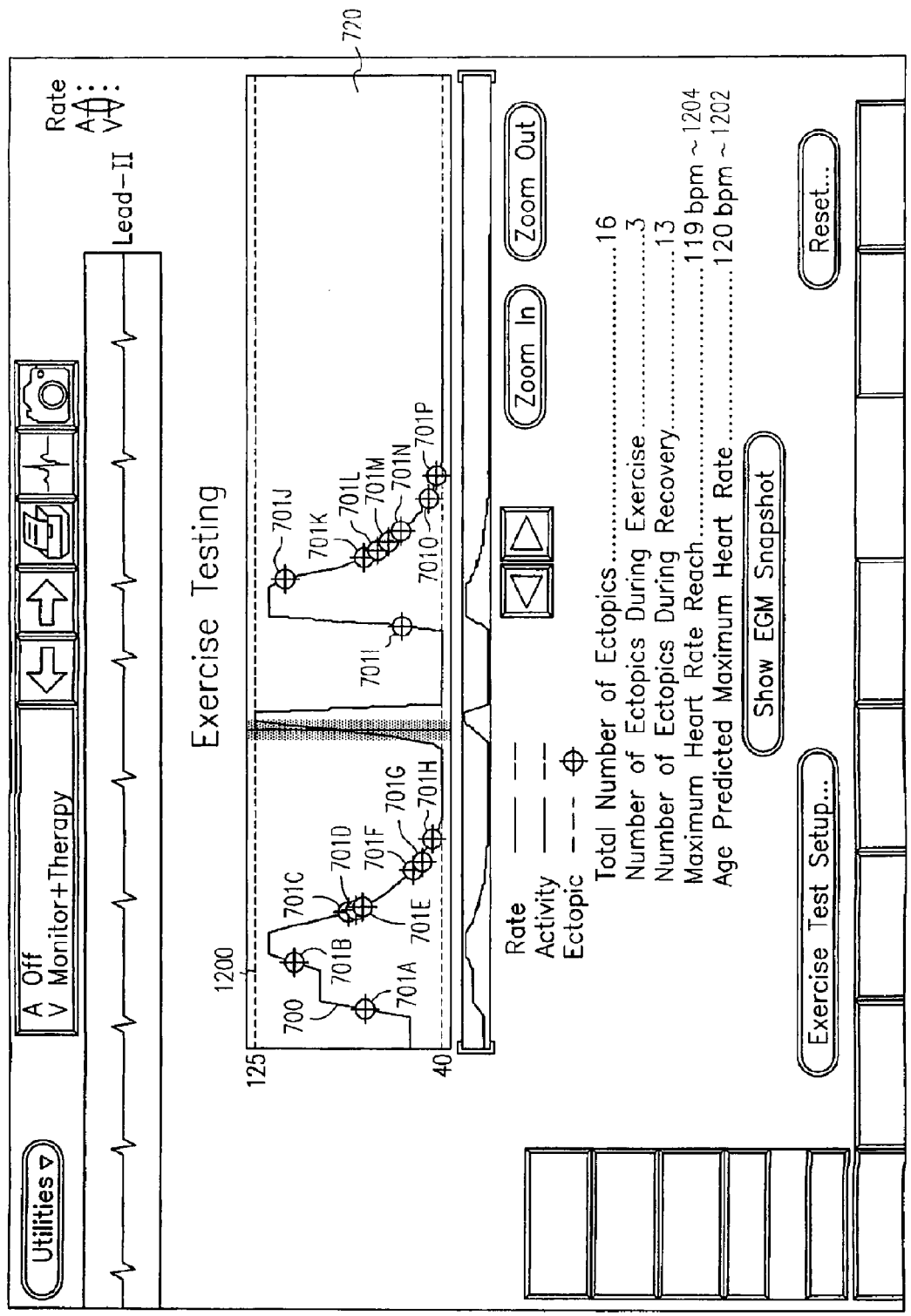
FIG. 12 is a screenshot illustrating generally another example of exercise episode summary information presented to a user via a display 226, and including information about age-predicted maximum heart rate and actually attained maximum heart rate.

FIG. 12 is a screenshot illustrating generally another example of exercise episode summary information presented to the user via the display 226, similar to FIGS. 7-11. In the example of FIG. 12, the window 720 displaying the graph 700 of heart rate vs. time also includes a line 1200 or other indicator of the patient's age-predicted maximum heart rate. The patient's age-predicted maximum heart rate is calculated by subtracting the patient's age in years from the number 220 (e.g., a 50 year old patient would have an age-predicted maximum heart rate of 220−50=170 beats per minute. In this example, the exercise episode summary information may also include a textual/alphanumeric indicator 1202 of the age-predicted maximum heart rate (e.g., 120 bpm in the example of FIG. 12) and a textual/alphanumeric indicator 1204 of the actual maximum heart rate attained by the patient during the exercise episode.

Figure 13:
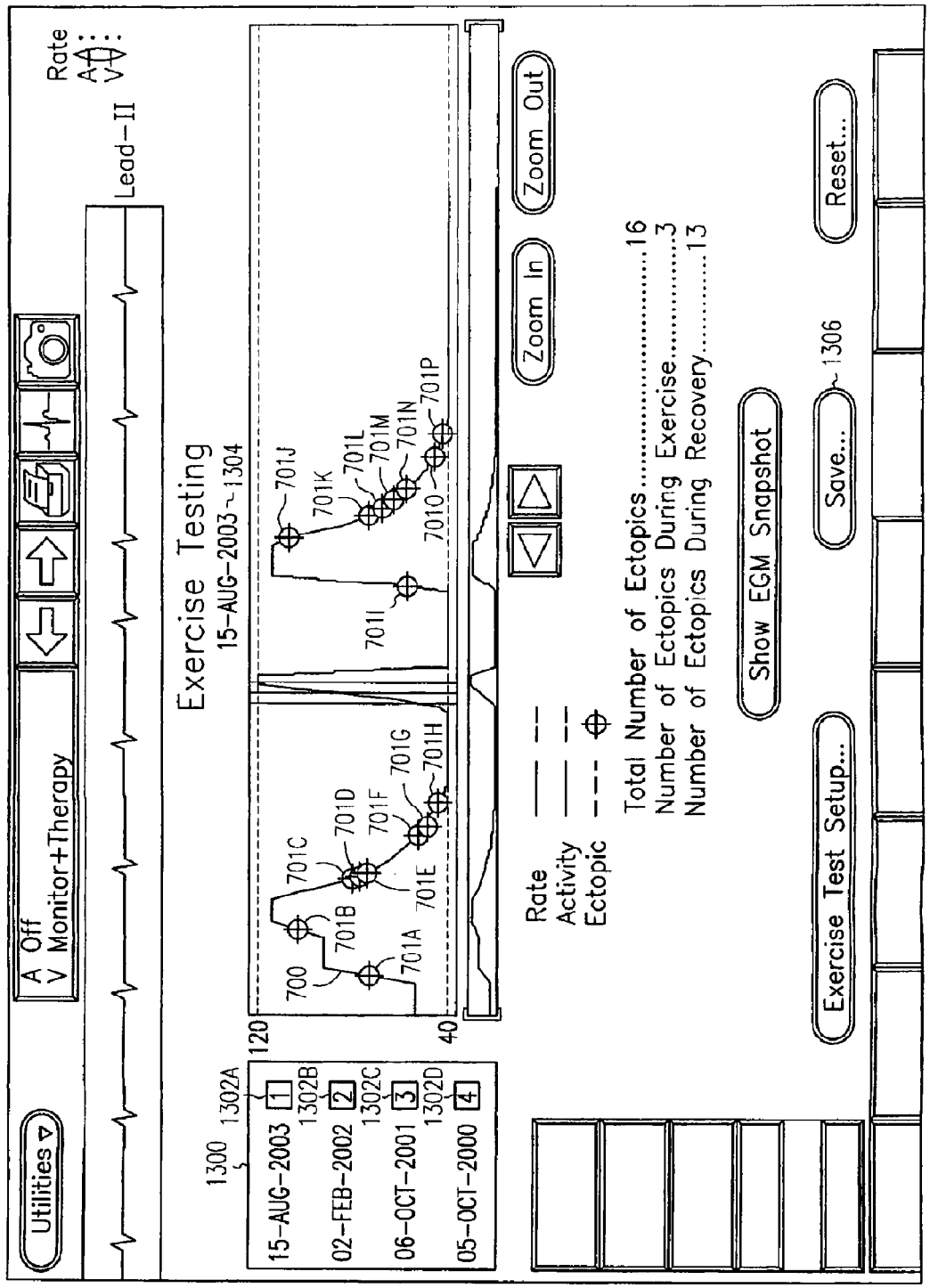
FIG. 13 is a screenshot illustrating generally another example of exercise episode summary information presented to a user via a display, and including a capability of storing and viewing multiple exercise episodes.

FIG. 13 is a screenshot illustrating generally another example of exercise episode summary information presented to the user via the display 226, similar to FIGS. 7-12. The example of FIG. 13 illustrates a capability of storing and viewing multiple exercise episodes. An episode menu 1300 identifies each such stored exercise episode, such as by using a timestamp/datestamp indicator 1302 to identify and distinguish the different exercise episodes. In one example, clicking on one of these indicators recalls the stored data for that episode for display in the exercise episode summary, together with the corresponding timestamp/datestamp indicator 1304 identifying which episode has been selected for display. In one example, such exercise episode data is automatically saved for each such exercise episode. In another example, such exercise episodes are manually saved and stored by the user, such as by clicking on a "Save" button 1306 to save and store the particular episode being displayed.

Figure 14:
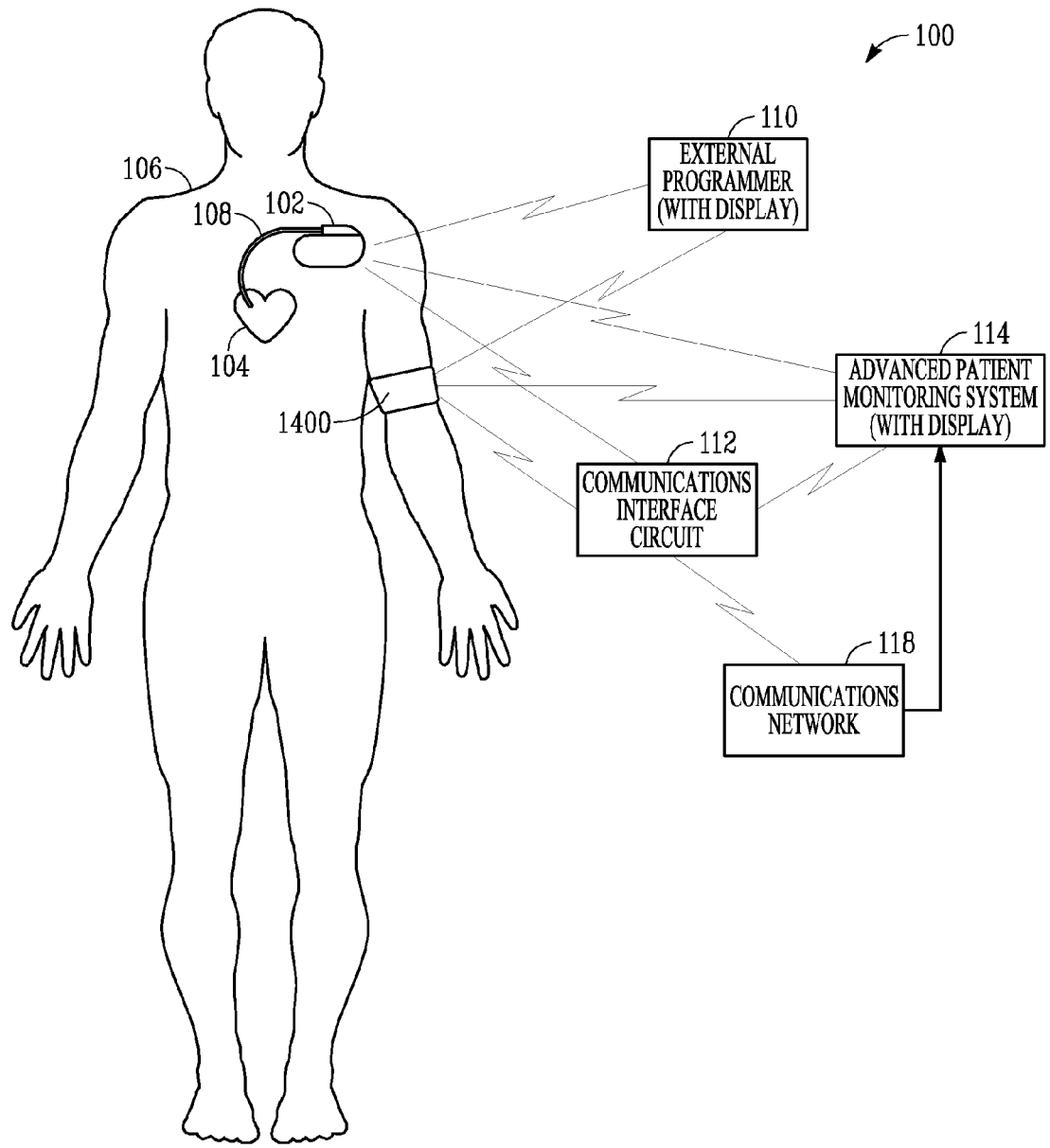
FIG. 14 is a schematic diagram illustrating generally another example of portions of a system including an exercise test interface, and further including a blood pressure monitor for monitoring the patient's blood pressure during the exercise test.

FIG. 14 is a schematic diagram, similar to FIG. 1, illustrating generally another example of portions of a system 100 including an exercise test interface, and further including a blood pressure monitor 1400 for monitoring the patient's blood pressure during the exercise test. In the example of FIG. 14, the blood pressure monitor is illustrated as an external cuff-style monitor 1400 that is communicatively coupled to one or more of the external programmer 110, the APM system 114, and/or the communications interface circuit 112. However, the blood pressure monitor 1400 could alternatively be an implantable blood pressure monitor (e.g., disposed on leadwire 108) that feeds blood pressure information to the implantable device 102 for communication from the patient. In one example, a graph of blood pressure vs. time or other blood pressure information during the exercise episode is displayed to the user in a similar manner to the displaying of metabolic need sensor output graph 800 in FIG. 8.

Figure 15:
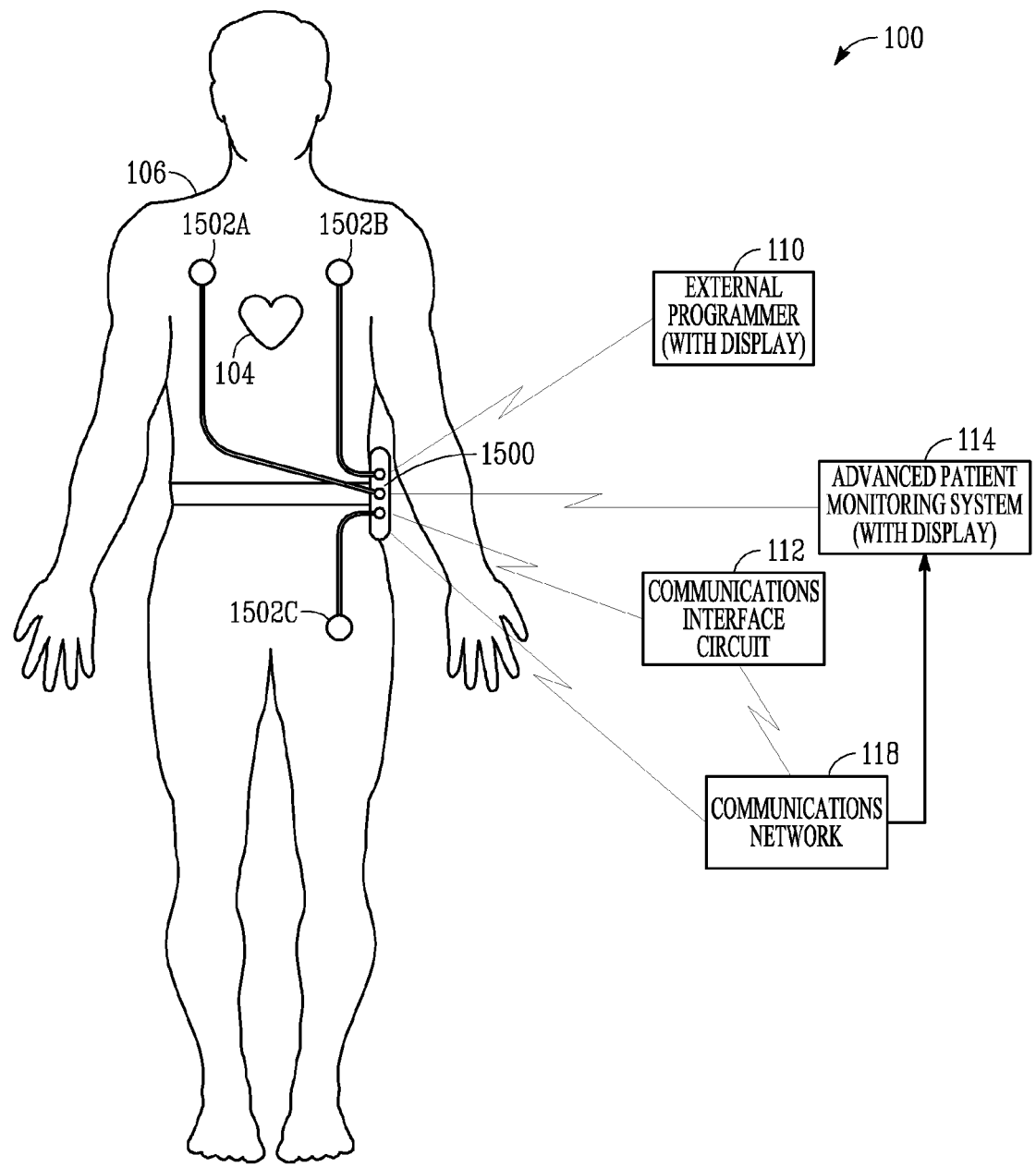
FIG. 15 is a schematic diagram illustrating an embodiment that need not use an implantable device.

FIG. 15 is a schematic diagram, similar to FIG. 1, but illustrating an embodiment that need not use an implantable device 102. Instead, heart rate information and/or activity (e.g., accelerometer) information is obtained from an external Holter-monitor-like device 1500 worn by the patient, e.g., clipped to the patient's belt. In this example an ECG signal is obtained from external electrode(s), such as skin electrodes 1502, which are connected to the device 1500. Such information is directly or indirectly communicated to an external device having a display, such as the external programmer 110 or the APM system 114, for providing an exercise episode summary as by using the techniques discussed above with respect to FIGS. 1-14.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. A system comprising:

a processor circuit, including at least one predetermined criteria configured to automatically identify, using physiological data obtained from a patient, a beginning and an end of an exercise episode of the patient, and including a data input circuit to receive episode data associated with the episode, wherein the processor circuit is configured to automatically extract at least one prognostic indicator from the episode data, the at least one prognostic indicator to include an indication of how many sequential runs of ectopic beats occurred during the episode, and wherein the processor circuit is configured to summarize the episode data;

a memory storage circuit, coupled to the data input circuit to store the data; and an external display, configured to display a summary of the episode data, the summary including the at least one displayed prognostic indicator automatically extracted from the episode data.

2. The system of claim 1, in which the episode includes an exercise period and a post-exercise recovery period.

3. The system of claim 1, in which the data input circuit receives heart rate data, and in which the at least one predetermined criteria includes at least one heart rate threshold that defines the episode for heart rates substantially continuously exceeding the at least one heart rate threshold.

4. The system of claim 1, in which the data input circuit receives activity sensor data, and in which the at least one predetermined criteria includes at least one activity sensor threshold that defines the episode for activity sensor levels that substantially continuously exceed the activity sensor threshold.

5. The system of claim 1, in which the processor includes a user-input circuit to receive at least one user-provided trigger identifying the episode.

6. The system of claim 1, in which the at least one displayed prognostic indicator includes an indication of how many ectopic beats occurred during the episode.

7. The system of claim 1, in which the at least one displayed prognostic indicator includes an indication of how many ectopic beats occurred during an exercise portion of the episode.

8. The system of claim 1, in which the at least one displayed prognostic indicator includes an indication of how many ectopic beats occurred during a post-exercise recovery portion of the episode.

9. The system of claim 1, in which the at least one displayed prognostic indicator includes an indication of how many sequential runs of ectopic beats occurred during an exercise portion of the episode.

10. The system of claim 1, in which the at least one displayed prognostic indicator includes an indication of how many sequential runs of ectopic beats occurred during a post-exercise recovery portion of the episode.

11. The system of claim 1, in which the at least one displayed prognostic indicator includes an indication of a rate of decrease of the patient's heart rate during a post-exercise recovery portion of the episode.

12. The system of claim 1, in which the at least one displayed prognostic indicator includes an indication of a maximum heart rate obtained by the patient during the episode.

13. The system of claim 12, in which the at least one displayed prognostic indicator includes an indication of an age-predicted maximum heart rate for the patient for comparison to the indication of the maximum heart rate obtained by the patient during the episode.

14. The system of claim 13, in which the at least one displayed prognostic indicator includes an indication of a comparison between the maximum heart rate obtained by the patient during the episode and the indication of the age-predicted maximum heart rate for the patient.

15. The system of claim 1, in which the at least one displayed prognostic indicator includes a resting heart rate associated with the episode.

16. The system of claim 1, in which the at least one prognostic indicator indicates an elevated value of the resting heart rate.

17. The system of claim 1, in which the at least one prognostic indicator includes an indication of heart rate variability associated with the episode.

18. The system of claim 1, in which the at least one prognostic indicator indicates a low heart rate variability.

19. The system of claim 17, in which the at least one prognostic indicator includes an indication of T-wave alternans associated with the episode.

20. The system of claim 1, in which the at least one prognostic indicator includes an indication of a heart rate corresponding to an onset of a T-wave alternans associated with the episode.

21. The system of claim 1, in which the at least one prognostic indicator includes an indication of heart rate turbulence associated with the episode.

22. The system of claim 1, in which the at least one prognostic indicator includes an indication of QT dispersion associated with the episode.

23. The system of claim 1, in which the at least one prognostic indicator includes an indication of paroxysmal atrial tachyarrhythmia associated with the episode.

24. The system of claim 1, in which the displayed summary includes a displayed graph of heart rate vs. time during at least a portion of the episode.

25. The system of claim 24, in which the graph includes an ectopic beat indicator associated with each ectopic beat occurring during the episode.

26. The system of claim 24, in which the graph includes an indication of the age-predicted maximum heart rate for the patient.

27. The system of claim 24, in which the graph includes a first indicator of at least one exercise period during the episode.

28. The system of claim 27, in which the graph further includes a second indicator of at least one post-exercise refractory period during the episode.

29. The system of claim 28, in which the first and second indicators include different background colors.

30. The system of claim 1, in which the summary includes a displayed graph of patient activity vs. time during the episode.

31. The system of claim 1, in which the summary includes a displayed heart electrical activity signal associated with the episode.

32. The system of claim 1, in which the processor is located in an implantable device.

33. The system of claim 1, in which the processor is located in an external device.

34. A system comprising:

a processor circuit, including at least one predetermined criteria configured to automatically identify, using physiological data obtained from a patient, a beginning and an end of an exercise episode of the patient, and including a data input circuit to receive episode data associated with the episode, wherein the processor circuit is configured to automatically extract at least one prognostic indicator from the episode data, the at least one prognostic indicator to include an indication of how many sequential runs of ectopic beats occurred during the episode; and wherein the processor circuit is configured to summarize the episode data;
- a memory storage circuit, coupled to the data input circuit to store the data; and
- means for displaying a summary of the episode data, including displaying the at least one displayed prognostic indicator automatically extracted from the episode.

35. The system of claim 34, in which the episode includes an exercise period and a post-exercise recovery period.

36. The system of claim 34, in which the data input circuit receives heart rate data, and in which the at least one predetermined criteria includes at least one heart rate threshold that defines the episode for heart rates substantially continuously exceeding the at least one heart rate threshold.

37. The system of claim 34, in which the data input circuit receives activity sensor data, and in which the at least one predetermined criteria includes at least one activity sensor threshold that defines the episode for activity sensor levels that substantially continuously exceed the activity sensor threshold.

38. The system of claim 34, in which the processor includes a user-input circuit to receive at least one user-provided trigger identifying the episode.

39. The system of claim 34, in which the at least one displayed prognostic indicator includes an indication of how many ectopic beats occurred during the episode.

40. The system of claim 34, in which the at least one displayed prognostic indicator includes an indication of how many ectopic beats occurred during an exercise portion of the episode.

41. The system of claim 34, in which the at least one displayed prognostic indicator includes an indication of how many ectopic beats occurred during a post-exercise recovery portion of the episode.

42. The system of claim 34, in which the at least one displayed prognostic indicator includes an indication of a rate of decrease of the patient's heart rate during a post-exercise recovery portion of the episode.

* * * * *